US009119796B2

(12) United States Patent
Cook et al.

(10) Patent No.: US 9,119,796 B2
(45) Date of Patent: *Sep. 1, 2015

(54) RAZOR COMPRISING A MOLDED SHAVING AID COMPOSITION COMPRISING A PYRITHIONE SOURCE

(75) Inventors: Jason Edward Cook, Anderson Township, OH (US); Chunpeng Jiang, Beijing (CN); Brian Joseph Limberg, Milford, OH (US); Edward Dewey Smith, III, Mason, OH (US); Juan Wang, Beijing (CN); Xiaoyong Wang, Beijing (CN)

(73) Assignee: The Gillette Company, Boston, MA (US)

( * ) Notice: Subject to any disclaimer, the term of this patent is extended or adjusted under 35 U.S.C. 154(b) by 560 days.

This patent is subject to a terminal disclaimer.

(21) Appl. No.: 13/406,913

(22) Filed: Feb. 28, 2012

(65) Prior Publication Data

US 2012/0216408 A1   Aug. 30, 2012

Related U.S. Application Data

(60) Provisional application No. 61/524,104, filed on Aug. 16, 2011.

(30) Foreign Application Priority Data

Feb. 28, 2011  (WO) ..................... PCT 2011/000320

(51) Int. Cl.
  *A61K 8/49*  (2006.01)
  *A61K 8/02*  (2006.01)
  *A61K 8/86*  (2006.01)
  *A61Q 9/02*  (2006.01)

(52) U.S. Cl.
  CPC ............. *A61K 8/4933* (2013.01); *A61K 8/0216* (2013.01); *A61K 8/86* (2013.01); *A61Q 9/02* (2013.01); *A61K 2800/87* (2013.01); *Y10T 29/49826* (2015.01)

(58) Field of Classification Search
  None
  See application file for complete search history.

(56) References Cited

U.S. PATENT DOCUMENTS

| 3,412,033 A | 11/1968 | Karsten et al. |
| 4,161,526 A | 7/1979 | Gorman |
| 4,345,080 A | 8/1982 | Bolich, Jr. |
| 4,482,715 A | 11/1984 | Trotz et al. |
| 4,818,436 A | 4/1989 | French et al. |
| 4,957,658 A | 9/1990 | French et al. |

(Continued)

FOREIGN PATENT DOCUMENTS

| DE | 19537509 A1 | 4/1997 |
| JP | 2001278863 | 10/2001 |

(Continued)

OTHER PUBLICATIONS

PCT International Search Report with Written Opinion in corresponding Int'l appln. PCT/US2012/026933 dated May 23, 2012.

(Continued)

*Primary Examiner* — Robert A Wax
*Assistant Examiner* — Melissa Mercier
(74) *Attorney, Agent, or Firm* — Ronald Terk Sia; Kevin C. Johnson; Steven W. Miller

(57) ABSTRACT

Razors comprising a shaving aid comprising a soap base and a pyrithione source.

16 Claims, 11 Drawing Sheets

(56) References Cited

U.S. PATENT DOCUMENTS

| | | | |
|---|---|---|---|
| 6,149,981 | A | 11/2000 | Chadwick et al. |
| 6,365,560 | B1 * | 4/2002 | Chopra et al. ............... 510/141 |
| 6,584,690 | B2 | 7/2003 | Orloff et al. |
| 7,703,361 | B2 | 4/2010 | Johnson et al. |
| 7,811,553 | B2 * | 10/2010 | O'Grady et al. ............... 424/73 |
| 2005/0118276 | A1 | 6/2005 | Lei et al. |
| 2006/0225285 | A1 | 10/2006 | Slavtcheff et al. |
| 2007/0009472 | A1 | 1/2007 | Niebauer et al. |
| 2008/0249136 | A1 | 10/2008 | Annis et al. |
| 2012/0103151 | A1 * | 5/2012 | Jones et al. ............... 83/22 |

FOREIGN PATENT DOCUMENTS

| | | |
|---|---|---|
| JP | 2008-1617 A | 1/2008 |
| JP | 2009-40819 A | 2/2009 |
| JP | 2010-100596 A | 5/2010 |
| KR | 20020036565 | 5/2002 |
| KR | 20020036565 * | 5/2014 |

OTHER PUBLICATIONS

Mintel: "Shaving Foam", GNPD, Jun. 1, 2008, XP002667882. Ducray Homme.

* cited by examiner

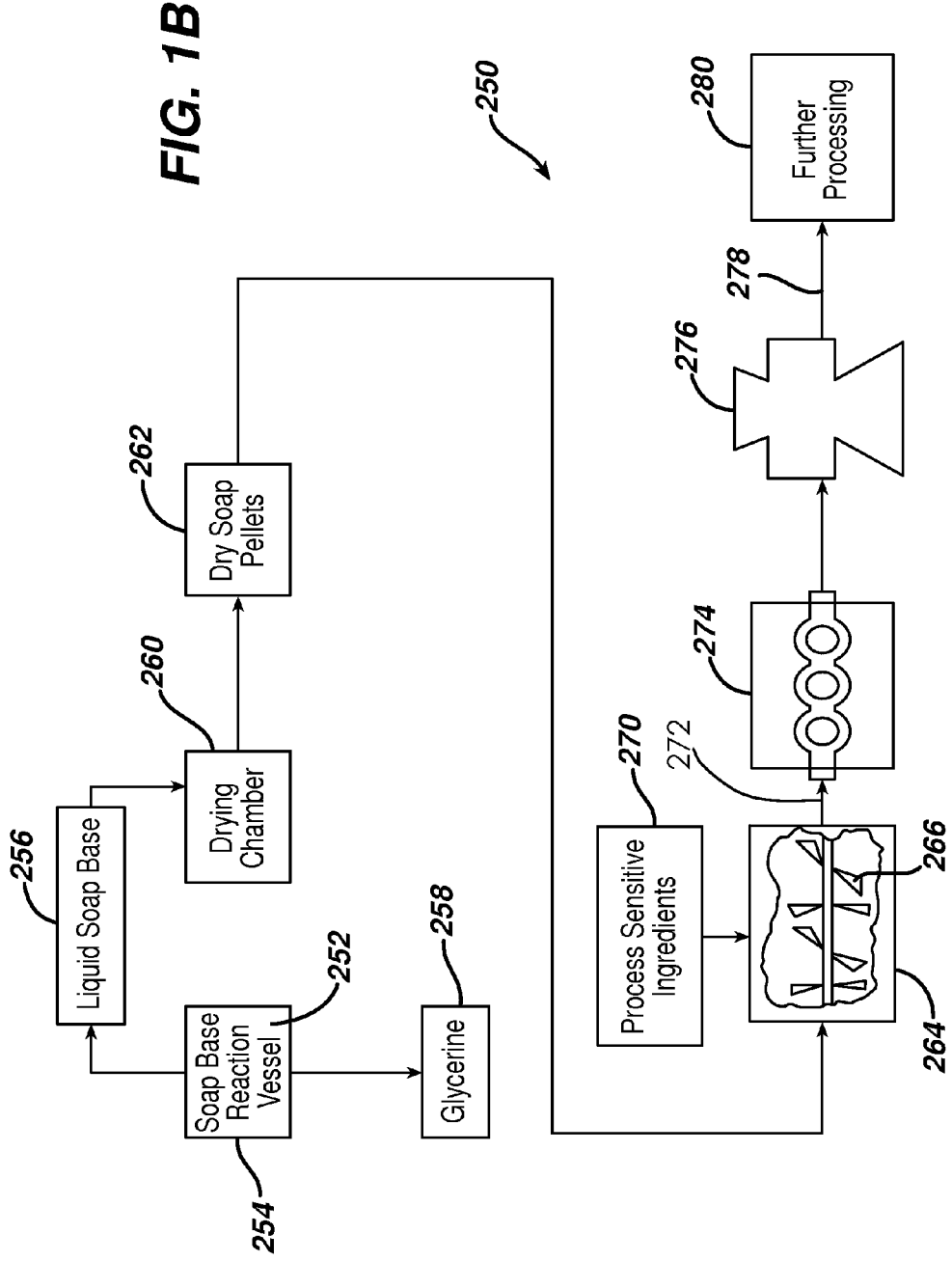

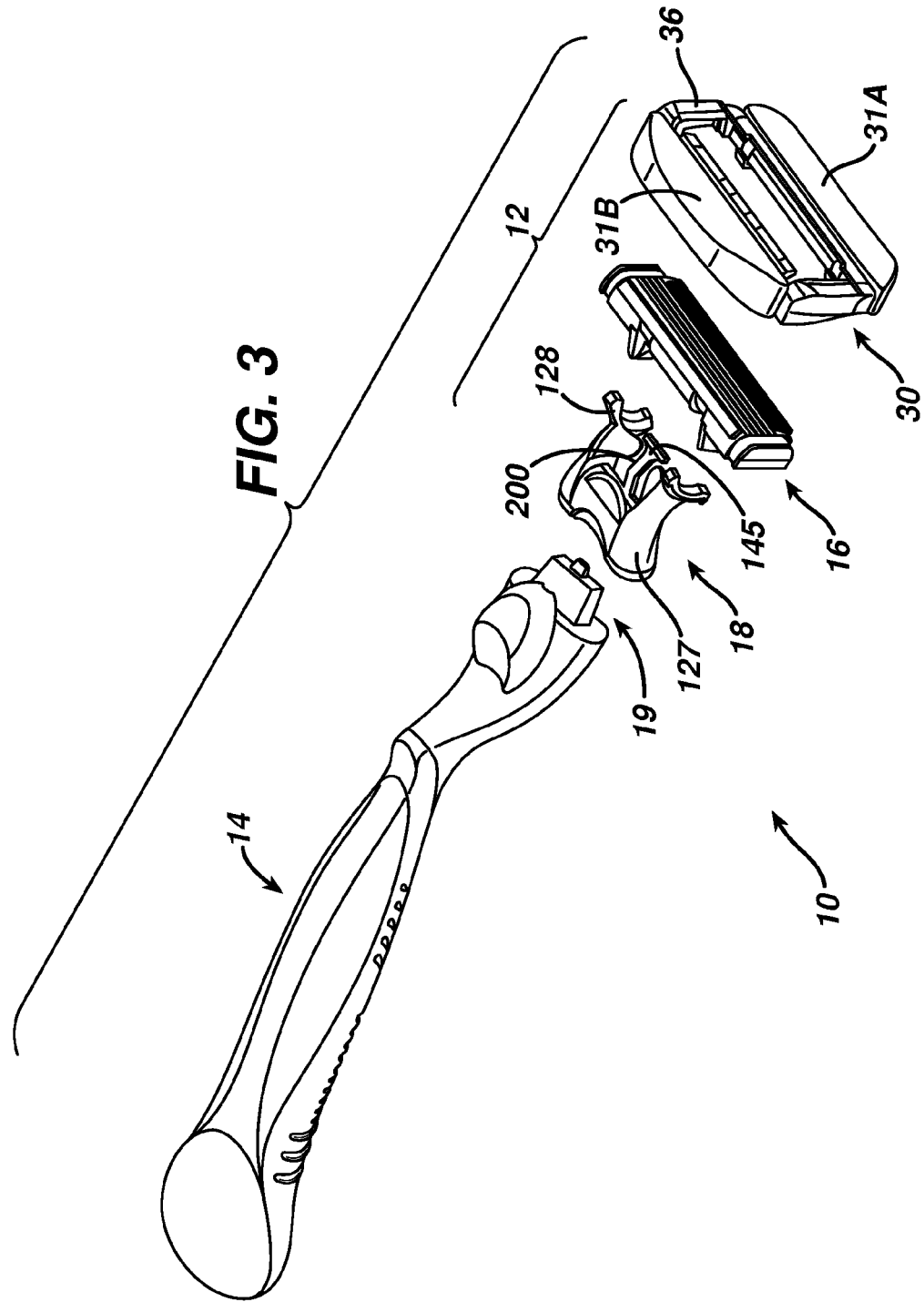

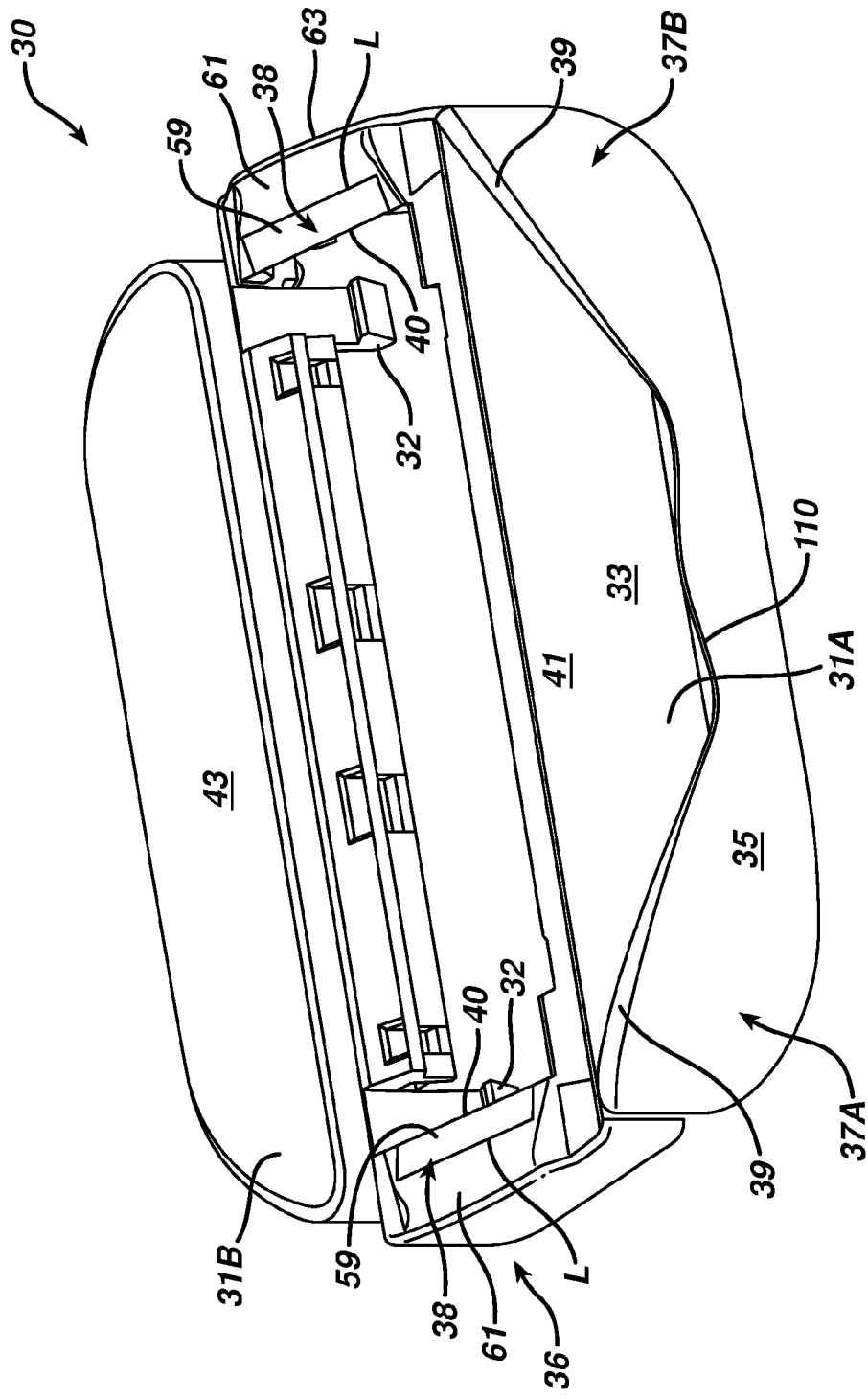

RAZOR COMPRISING A MOLDED SHAVING AID COMPOSITION COMPRISING A PYRITHIONE SOURCE

CROSS REFERENCE TO PENDING APPLICATIONS

This application claims the benefit of U.S. Provisional Application No. 61/524,104 filed on Aug. 16, 2011, U.S. application Ser. No. 13/036,889 filed on Feb. 28, 2011 and PCT China Application No. CN2011/000320, case number AA00812F, filed on Feb. 28, 2011.

BACKGROUND

Providing soap mounted on a razor handle or cartridge is known. For example, U.S. Pat. No. 6,584,690 describes a razor that carries a shaving preparation, e.g., in the form of a solid cake of soap that surrounds the cartridge. Further 2-in-1 razors are not new and have also been marketed under the Venus Breeze® line of razors and the Schick® Intuition® line of razors. See also US Patent Publ Nos. 2006/225285A and 2006/080837A, and U.S. Pat. No. 7,811,553.

Addition of pyrithione sources, such as zinc pyrithione, into soap bars for antibacterial purposes has been described. See e.g. US 2008/0249136 A1. The zinc pyrithione ("ZPT") can be added in the form of small or fine particles. Antibacterial bar soap including ZPT are often used because the surfactancy of the soap is believed to help in removal of microbial entities or microbials on the skin, while the antimicrobial agent such as the ZPT can deposit onto skin to provide residual protection against subsequent invasion.

One problem with the introduction of pyrithione source into soap bars is that during manufacturing, handling or storage of a bar soap, various metallic parts of the manufacturing equipment, for example pipes, nozzles may be contacted with the bar soap. In some situation, such contact can maintain a long time (e.g. overnight to 24 hours), and at a relatively elevated temperature. Such contact has the potential of causing a color change of the bar soap, so called "discoloration", which is from a colored precipitate. A number of solutions toward this pyrithione discoloration problem have been described. For example, in U.S. Pat. No. 4,161,526, JP Patent Publication 2001-278863A, U.S. Pat. Nos. 4,482,715, 4,957,658 and 4,818,436.

Although the addition of pyrithione sources into bar soaps is believed to provide antibacterial benefits in a washing context, the use of bar soaps in a shaving context has encountered other complexities. In particular, when skin is shaved with a razor cartridge, the razor blades can remove most if not all items present on the skin, such as, removing hairs, surface skin cells, shaving preparations, soap residue, skin care actives and any other ingredients or actives present on the skin before contacting the blades. As such, there remains a need to deliver antibacterial benefits such as those from antibacterial soaps in a shaving context, and preferably while avoiding discoloration issues.

SUMMARY

One aspect of the present invention relates to a shaving cartridge comprising: a housing having a front edge and a rear edge; one or more shaving blades between the front edge and the rear edge; a shaving aid holder; and at least one shaving aid portion mounted on the shaving aid holder, the shaving aid portion comprising from about 0.1% to about 10 wt % polyoxyethylene, a soap base, and a pyrithione source. Depending on the order in which ingredients are added, the pyrithione source can be present in the soap base prior to introduction into the shaving aid, and/or it can be a direct add into the shaving aid mixture. The pyrithione source can be a zinc pyrithione (ZPT) in varying form, such as a platelet, and optionally a pH adjuster can be added to the soap base and/or shaving aid. In one aspect of the invention, the shaving cartridge comprises two shaving aid portions, one positioned forward of the blades (in the vicinity of the forward edge) and one positioned aft of the blades (in the vicinity of the rear edge). One or both of these shaving aid portions can comprise a pyrithione source. The shaving aid portions can be the same formula or different, for example the pyrithione source can just be present in the shaving aid portion aft of the blades if that is desired.

In one embodiment, the shaving aid comprising a pyrithione source, a soap base, and a pH adjusting agent selected from a group consisting of ammonia solution, triethanolamine, diethanolamine, monoethanolamine, potassium hydroxide, sodium hydroxide, soluble carbonate salts, and combinations thereof, wherein said soap attains a pH of greater than or equal to 10.7.

In another embodiment, the shaving aid comprises: (a) from about 0.1% to about 35%, by weight of shaving aid, of water; (b) from about 45% to about 99%, by weight of shaving aid, of soap; (c) from about 0.01% to about 5%, by weigh of shaving aid, of platelet zinc pyrithione (platelet ZPT), wherein the platelet ZPT comprises a mean particle diameter of about 0.5 microns to about 10 microns, a median particle diameter of about 0.5 microns to about 10 microns, and a thickness of about 0.6 microns to about 15 microns.

Another aspect of the present invention provides for a method of making shaving cartridge comprising a molded shaving aid portion, the method comprising: heating a soap base to a temperature sufficient to melt the soap base; adding a pyrithione source to the soap base melt to form a shaving aid composition; cooling the shaving aid composition to form a shaving aid portion; and attaching the shaving aid portion to said shaving cartridge.

DESCRIPTION OF DRAWINGS

FIG. 1B is a diagram of a process of forming a molded shaving aid composition utilizing an extruded soap base.

FIG. 3 is an exploded perspective view of the razor of FIG. 1.

FIG. 4A is a perspective view of the holder portion of the cartridge shown in FIG. 1, viewed from above.

Like reference symbols in the various drawings indicate like elements.

DETAILED DESCRIPTION

Figure 1A:
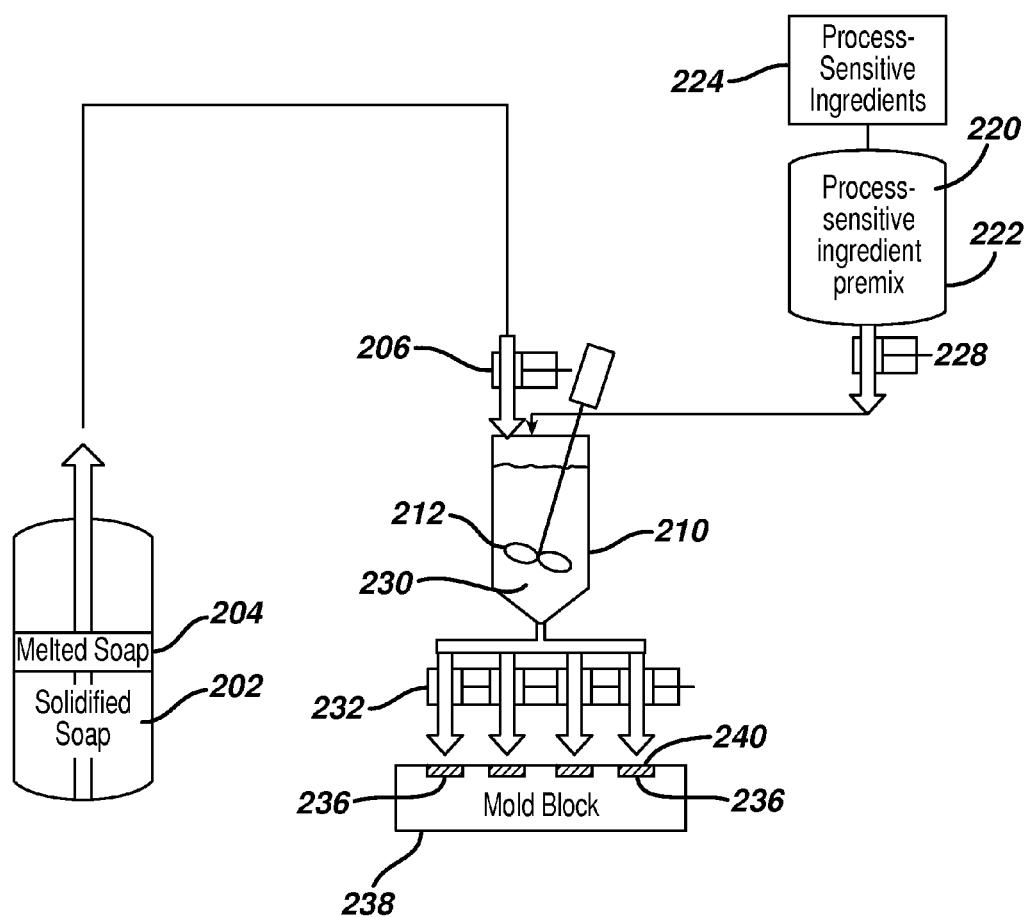
FIG. 1A is a diagram of a process of forming a molded shaving aid composition utilizing a poured soap base.

Razors having shaving aid compositions that are soap based can be used without the need for a separate shaving aid, such as, e.g., bar soap, shaving cream or gel. This can simplify razor usage, for example, by permitting shaving in the shower without the need for continued reapplication of the shaving aid to the skin. It has been recently found to be desirable to add a pyrithione source to the shaving aid and/or the soap base to provide various benefits which will be described in more detail herein.

Generally, the shaving aid composition can be formed by first obtaining (e.g., making) a soap base, e.g., an extruded soap base or a poured soap base. Process-sensitive ingredients, which can include pyrithione sources, can be incorporated into the soap base to form a shaving aid composition. In some instances, however, the pyrithione source can be selected and formed such that is can be added at any point during the making of the shaving aid composition or soap base. Generally, if the soap base is a poured soap base, this is achieved by melting the poured soap base, adding the process-sensitive ingredients, and then cooling the resultant composition, for example, by placing into a mold and cooling the composition, within a period of time in which the process-sensitive ingredients remain substantially non-degraded, e.g., within about 1 hour. Where the soap base is an extruded soap base, the soap base and the process-sensitive ingredients are combined by milling, grinding, and/or other mixing techniques, refined, and extruded to form a shaving aid composition. Additionally, a good quality shaving aid composition can be achieved by avoiding remelting of the process-sensitive ingredients.

In one embodiment, the shaving cartridge comprises a housing having a front edge and a rear edge, one or more shaving blades between the front edge and the rear edge, and a shaving aid holder. The cartridges include at least one shaving aid portion mounted on the shaving aid holder. The shaving aid portion includes from about 0.1 to about 10 wt % or 1 wt % to about 5 wt % of a polyoxyethylene, a pyrithione source, and a molded or extruded soap base.

In one embodiment, the soap base comprises from about 45% to about 99% of a soap and from about 0.01% to about 5% a pyrithione source. The pyrithione source can be ZPT, and can even be in the form of a platelet. The platelet ZPT has a median particle diameter of about 0.5 microns to about 10, alternatively about 1 to about 5 microns, and alternatively about 3 microns; a mean particle diameter of about 0.5 to about 10 microns, alternatively about 1 to about 5 microns, alternatively about 2 to about 4 microns, and alternatively about 3 microns, and a thickness of about 0.6 to about 15 microns, alternatively about 0.6 to 1 micron, alternatively about 0.6 to about 0.8, and alternatively about 0.6 to about 0.7 microns. The platelet ZPT can also have a span of less than about 5, and alternatively about 1.

Without wishing to be bound by theory, it is believed that the use of platelet ZPT improves the antimicrobial efficacy of the soap base on skin, and, thus, can improve protection against subsequent invasion of microbials on skin. In particular, the number of microbials that can form on the surface after use of a composition comprising platelet ZPT is believed to be reduced. Additionally, the efficiency on, for example, a mass basis of the amount of ZPT deposited on the surface after use of the composition comprising platelet ZPT is improved. As such, the overall residual efficacy of the compositions is believed to be also improved resulting in improved protection from subsequent invasions of microbials on the surface.

In one embodiment, a pH adjusting agent can be included to provide the advantages of avoiding potential discoloration of the soap base or shaving aid. This can be particularly desirable if the shaving aid is white or has limited colorants. Low to nil levels of ingredients such as fragrance and colorants can be desirable so in these cases, avoiding discoloration can provide enhanced product shelf and use life. As such, in one embodiment, the shaving aid is free or substantially free (i.e. no amount of such ingredient is intentionally added but trace amounts for processing conditions can be present) of colorant and/or fragrances.

The polyoxyethylene can have a molecular weight of from about 100,000 to about 5,000,000. The shaving aid composition can further include a silicone polymer (e.g., from about 0.25 wt % to about 5 wt % silicone polymer). The shaving aid composition can further include a polyethylene, polybutene, and mineral oil composition. The composition can include from about 0.25 wt % to about 5 wt % silicone polymer, from about 10 wt % to about 60 wt % fatty acid salts, from about 0.1 wt % to about 8 wt % esters, from about 0.25 wt % to about 10 wt % polyoxyethylene and from about 0.3 wt % to about 10 wt % of a polyethylene, polybutene and mineral oil composition. The soap base can be a poured soap base, an extruded soap base, or a combination thereof.

Optional wear enhancing ingredients can increase the wear resistance of the shaving aid composition (as compared with a shaving aid composition lacking the wear enhancing ingredients), such that the shaving aid composition lasts through a greater number of shaves and/or so that the shaving aid composition does not rapidly dissolve or disintegrate in the presence of water. Many wear enhancing ingredients are process-sensitive. Many other desirable ingredients, for example, moisturizers, fragrances, and the like, may similarly be process-sensitive. Methods are provided that allow for the incorporation of such process-sensitive ingredients into a molded soap-based shaving aid composition.

I. Pyrithione Source

As used herein, the pyrithione source can be a pyrithione and a pyrithione salt capable of providing antimicrobial efficacy and/or other aesthetic and shave benefits. Preferred pyrithione salts are those formed from heavy metals such as zinc, tin, cadmium, magnesium, aluminum and zirconium Zinc salts are most preferred, especially the zinc salt of 1-hydroxy-2-pyridinethione (zinc pyridinethione, also named zinc pyrithione, ZPT). Other cations such as sodium may also be suitable. The pyrithione source may be selected from the group consisting of sodium pyrithione, zinc pyrithione, magnesium disulfide pyrithione, pyrithione acid, dipyrithione, chitosan pyrithione and combinations thereof. Preferably, it is sodium pyrithione or zinc pyrithione and more preferably, it is a zinc pyrithione (ZPT). ZPT is commercially available from various suppliers. For example, ZPT FPS available from Arch Chemical can be used. It is an aqueous dispersion comprising 48% active ZPT.

Pyrithione sources are well known in the personal cleansing art, and are described, for example, in U.S. Pat. Nos. 2,809,971; 3,236,733; 3,753,196; 3,761, 418; 4,345,080; 4,323,683; 4,379,753; and 4,470,982. Descriptions about pyrithione sources in the above mentioned patents are incorporated herein by reference. The pyrithione source can be present in the shaving aid composition in an amount ranging from about 0.05%, 0.1% or 0.4% to about 0.5%, 1%, 2% or 5% by weight.

Zinc Source

The shaving aid composition may additionally comprise a zinc source at a level of from about 0.01% to about 0.5%, by weight. Suitable zinc source include those zinc-containing materials described in U.S. Pat. No. 4,161,526, which can also provide discoloration inhibiting benefit. Specifically, the zinc source is selected from a group consisting of a zinc salt of an organic carboxylic zinc salt, inorganic zinc salt, zinc hydroxide, zinc oxide, and combinations thereof. In one embodiment, the zinc source is zinc carbonate and/or zinc oxide. The zinc source, for example, zinc carbonate is also known as being able to potentiate the efficacy of the pyrithione source. In one embodiment, the shaving aid comprises 0.5% zinc pyrithione, 2% sodium carbonate, and 0.1% zinc carbonate.

Zinc Pyrithione

According to an example embodiment, the shaving aid can further comprise a pyrithione or a polyvalent metal salt of pyrithione such as a zinc salt of 1-hydroxy-2-pyridinethione (known as "zinc pyrithione" or "ZPT").

In a preferred embodiment, the zinc pyrithione included in soap base is dry powder zinc pyrithione in platelet particle form ("platelet ZPT"). According to example embodiments, the platelet ZPT included in the soap base composition can include particles with, for example, a median particle diameter of about 0.5 microns to about 10, alternatively about 1 to about 5 microns, and alternatively about 3 microns and a mean particle diameter of about 0.5 to about 10 microns, alternatively about 1 to about 5 microns, alternatively about 2 to about 4 microns, and alternatively about 3 microns. The platelet ZPT can also have a thickness of about 0.6 to about 15 microns, alternatively about 0.6 to about 1 micron, alternatively about 0.6 microns to about 0.8 microns, and alternatively about 0.6 microns to about 0.7 microns as shown in FIG. 1 of U.S. patent Ser. No. 13/036,889, Smith et al. filed on Feb. 28, 2011, Application Docket No. 12005. The platelet ZPT included in the shaving aid can also have a span of less than about 5, and alternatively about 1.

The shaving aid can include from about 0.01% to about 5%, by weight of the bar composition, of platelet ZPT, alternatively from about 0.1% to about 2%, and alternatively from about 0.1% to about 1%. The platelet ZPT can be included in the shaving aid as a dry powder that is, for example, dispersed with the soap ingredients. Alternatively, the platelet ZPT can be included in the shaving aid as aqueous dispersion with, for example, in the soap base.

In one embodiment, the platelet ZPT can be stabilized against, for example, flocculation. In one embodiment, each of the platelet ZPTs can have a coating or layer thereon to prevent the platelet ZPTs from attaching to each other. The coating or layer can be polynaphthalene sulfonate or any other suitable sulfate, sulfonate, carboxylate, or other compound that provides stability for example by charge or steric barrier.

In example embodiments, the ZPT can be made by reacting 1-hydroxy-2-pyridinethione (i.e., pyrithione acid) or a soluble salt thereof with a zinc salt (e.g. zinc sulfate) to form a zinc pyrithione precipitate as illustrated in U.S. Pat. No. 2,809,971 and the zinc pyrithione can be formed or processed into platelet ZPT using, for example, sonic energy as illustrated in U.S. Pat. No. 6,682,724.

It has been discovered that the use of platelet ZPT in a shaving aid or soap base provides improvements in the efficiency of the amount of ZPT deposited on the surface upon which the razor and shaving aid(s) is being used on as well as reductions in the amount of antimicrobials that form after use.

More specifically, it has been discovered that the use of platelet ZPT having a median particle diameter of about 1 micron to about 5 microns, a mean particle diameter of about 1 microns to about 5 microns, and a thickness of about 0.6 microns to about 15 microns provides improvements in the efficiency of the amount of ZPT deposited on the surface upon which the razor cartridge and shaving aid(s) are being used on as well as reductions in the amount of antimicrobials that form after use in comparison with, for example, particulate ZPT such as the particulate ZPT shown and explained in FIG. 2 of U.S. patent Ser. No. 13/036,889, Smith et al. filed on Feb. 28, 2011. Further, FIG. 3 of U.S. patent Ser. No. 13/036,889 illustrates these improvements by comparing an antimicrobial soap bar composition that includes particulate ZPT having a median particle diameter of about 0.70 microns, a mean particle diameter of about 0.75 microns, and a thickness of less than 0.6 microns with an antimicrobial soap bar composition that includes platelet ZPT described above. As shown in FIG. 1 of U.S. patent Ser. No. 13/036,889, the use of platelet ZPT reduces the number of colony forming units (CFUs) that form on a substrate in comparison with particulate ZPT. As such, the use of platelet ZPT increases the antimicrobial/antibacterial residual efficacy of the shaving aid and provides protection on the surface the antimicrobial bar composition is used on from subsequent invasions of microbials.

II. Soap Base

The shaving aid composition includes a soap base, e.g., a poured soap base or an extruded soap base. The basic component of the soap base can be a vegetable oil or tallow, saponified or neutralized to form the base, or can be a synthetic poured soap base. Super-fatted materials containing portions (e.g., greater than about 25 weight percent) of coconut acid or other fatty acids may also be used. In some embodiments, the shaving aid composition includes a base comprising a vegetable oil or a tallow or the like, or a combination of the foregoing materials, which is saponified or neutralized. The saponification or neutralization of the vegetable oil or tallow results in the production of glycerol and salts of fatty acids to form the base. The shaving aid composition can include about 50 wt % to about 100 wt % saponified or neutralized base (e.g., about 75 wt % to about 100 wt % saponified or neutralized base), which may be opaque, translucent, or transparent. Exemplary salts of fatty acids that may be produced include sodium carboxylate salts having up to about 22 carbon atoms.

The soap base can be a synthetic soap base. In certain embodiments, the synthetic soap base includes a glycol (e.g., diproylene glycol, propylene glycol, tripropylene glycol, and/or methylpropane diol glycol), glycerin, fatty acid salts (e.g., sodium stearate and/or potassium stearate), C15-C25 alcohols (e.g., behenyl alcohol, stearyl alcohol, cetyl alcohol, and/or myristic alcohol), steareth (e.g., a steareth 21 such as, for example, Brij®-721), stearic acid, microcrystalline wax (e.g., microcrystalline wax SP 16, SP 19, SP 16, SP 18, SP-1674, SP 16W, SP 60W, SP 89, Multiwax 180M, X-145, W-445, and/or W-835), one or more surfactants (e.g., Tegobetaine F-50, Lonzaine®, the Mackam® family of surfactants, the Mirataine® family of surfactants, and sodium lauryl ether sulfate ("SLES") (e.g., 25% active SLES). In some embodiments, glycerin is not included in the soap base. Glycerin can optionally be included, in part or in whole, in a process sensitive phase described in greater detail below.

The soap base can, in certain embodiments, include from about 0.5% to about 30% glycol (e.g., from about 10% to about 25% glycol or from about 12% to about 15% glycol), from about 10% to about 40% glycerin (e.g., from about 18% to about 34% glycerin or from about 18% to about 24% glycerin), from about 20% to about 40% fatty acid salt (e.g., from about 25% to about 40% fatty acid salts (e.g., stearate) or from about 30% to about 35% fatty acid salt), from about 0.1% to about 10% stearic acid (e.g., from about 2 to about 5% stearic acid), from about 0.5% to about 10% microcrystalline wax (e.g., from about 0.5% to about 5% microcrystalline wax or from about 1% to about 3% microcrystalline wax), from about 1% to about 15% betaine (e.g., from about 2% to about 10% active betaine or from about 4% to about 9% active betaine), and from about 1 to about 20% active SLES (e.g., from about 1% to about 20% active SLES or from about 10% to about 15% active SLES), all based on the weight of the poured soap base. One exemplary poured soap base prior to addition of the pyrithione source includes the following:

| | |
|---|---|
| Dipropylene glycol | 17.2% |
| Glycerin | 21.4% |
| Sodium stearate | 34.4% |
| Stearic acid (Pristerene ® 4980) | 3.7% |
| Microcrystalline wax SP 89 | 1.2% |
| Tegobetaine F-50 | 7.4% |
| SLES, 25% active | 14.7% |

In some embodiments, a combination of base and synthetic surfactants can be employed.

Additional Antibacterial Agents

The soap base can optionally further include one or more additional antibacterial agents that can serve to further enhance the antimicrobial effectiveness of the bar compositions. When present, the antimicrobial bar composition can include from about 0.001% to about 2%, preferably from about 0.01% to about 1.5%, more preferably from about 0.1% to about 1%, by weight of the antimicrobial bar composition. Examples of antibacterial agents that can be employed are the carbanilides, for example, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid and other organic acids. Other suitable antibacterial agents are described in detail in U.S. Pat. No. 6,488,943 (referred to as antimicrobial actives).

pH and pH Adjusting Agents

In one embodiment, the pH of the present soap base is greater than or equal to 10.7, preferably greater than or equal to 11, 11.5, 12, 12.5, 13, and 13.5, till up to 14. As used herein, pH of the present composition is measured at around 25° C. using any commercially available pH meter. When the tested composition is in a solid form, it is first dissolved in distilled water to form an aqueous solution of a concentration of 10%. The pH of this aqueous solution is then tested to be representative of the soap base.

In one embodiment, the present soap base comprises a pH adjusting agent in a sufficient amount to attain the above mentioned pH. The pH adjusting agents useful for the present composition includes alkalizing agents. Suitable alkalizing agents include, for example, ammonia solution, triethanolamine, diethanolamine, monoethanolamine, potassium hydroxide, sodium hydroxide, sodium phosphate dibasic, soluble carbonate salts, ammonia solution, triethanolamine, diethanolamine, monoethanolamine, potassium hydroxide, sodium hydroxide, sodium phosphate dibasic, soluble carbonate salts and combinations thereof.

The amount of the pH adjusting agent required to attain the requisite pH can be calculated by one skilled in the art following known chemical parameters, for example, pKa value of the pH adjusting agent.

In one embodiment of the present invention, the present soap base comprises a soluble carbonate salt presented in an amount effective to attain a pH of greater than or equal to 10.7 to decrease discoloration. Soluble carbonate salts may include those carbonates and bicarbonates that have a solubility of greater than or equal to 0.01 g in water at 20° C. Such carbonates can be selected from a group consisting of sodium carbonate, potassium carbonate, ammonium carbonate, aluminum carbonate, magnesium carbonate, sodium bicarbonate, potassium bicarbonate, ammonium bicarbonate and combinations thereof.

In another embodiment, the present composition comprises a soluble carbonate salt in an amount effective to prevent discoloration. For example, soluble carbonate salt is present in the present composition in an amount ranging from about 0.3%, 0.5%, 0.8%, 1% or 1.5% to about 2%, 2.5%, 5%, 10% or 20%.

In one embodiment where the soap base comprises a pyrithione source and a soap surfactant, the soap base can also comprise a pH adjusting agent selected from a group consisting of ammonia solution, triethanolamine, diethanolamine, monoethanolamine, potassium hydroxide, sodium hydroxide, sodium phosphate dibasic, soluble carbonate salts and combinations thereof, wherein the soap attains a pH of greater than or equal to 10.7. This soap base shows a decreased discoloration and comparative examples are provided in FIG. 1 of PCT China Patent Serial No. CN2011/000320, Smith et al. filed on Feb. 28, 2011. Without being bound by theory, it is believed that by increasing the pH, a configuration change of the pyrithione group happens, making the pyrithione group tend not to react with the dissolved ferric or cupric ions to form colored precipitates, thereby inhibiting or decreasing discoloration.

Specifically, pyrithione, i.e., 1-hydroxy-2-pyridinethione, is an aromatic heterocycle related to pyridine as shown in Formula 1.

(1)

Via the sulfur and the oxygen of its N-hydroxythioamide group, it forms a complex (as shown in formula 2) with a transitional metal, which may be selected from the group consisting of zinc ion, ferric ion and cupric ion, but is not limited to these. The chemical structure of the N-hydroxythioamide group in the pyrithione anion species gives rise to a bidentate character due to the negative charge and the adjacent strong electron donor potential, and it is this allowing the coordination with metal cations such as zinc, copper or ion.

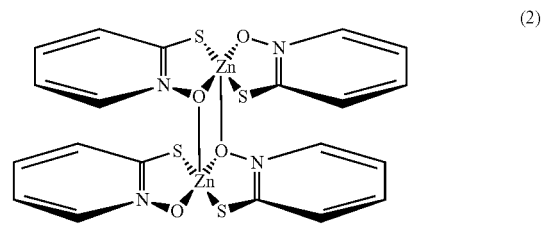

(2)

According to Irving & Williams Series, the smaller an ionic radius is, the more stable of the coordination between pyrithione and the metal ion. $Fe^{3+}$ has a radius of 0.64 A which is smaller than that of $Cu^{2+}$ 0.73 A, and which in turn is smaller than that of $Zn^{2+}$ 0.74 A. This helps explain the formation of undesired pyrithione discoloration in the existence of other pyrithione source, such as zinc pyrithione.

However, due to tautomerism and acid-base equilibria, pyrithione is subject to speciation, as shown in equilibrium scheme (I).

Equilibrium Scheme (I)

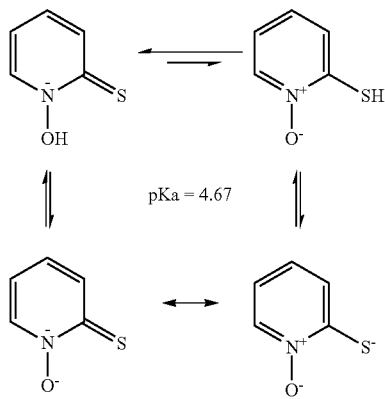

It is believed by the present inventor that an increased pH plays a role in turning the equilibrium of the pyrithione speciation from the pyrithione carrying a positively charged nitrogen atom (shown in the equilibrium scheme II below on the right) to a negatively charged nitrogen atom (shown in the equilibrium scheme II below on the left). The pyrithione speciation on the left of the equilibrium scheme II is incapable of coordinating with metal ion including ferric ion. Free ferric ions can then turn into $Fe(OH)_3$ and finally $Fe_2O_3$ under increased pH condition, and further prevent the formation of undesired colored ferric pyrithione.

Equilibrium Scheme (II)

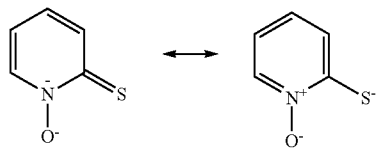

Discoloration

As used herein, "discoloration" means the color change brought by colored precipitates formed from a reaction of pyrithione source with unwanted dissolved metal ions, such as ferric ions and/or cupric ions. The discoloration can be in a color of grayish blue, blue, black, purple, green and the other colors, which are different from an original color of a soap base comprising a pyrithione source. By "original color", it means the color of the soap base before the pyrithione source in the bar reacts with ferric and/or cupric ion. A number of ways are available for measuring discoloration. Details of measurement are described in later section of the present specification under Discoloration Test Method.

III. Methods of Making the Molded Shaving Aid Composition

Multi-Step Process

In one embodiment, the shaving aid is molded and can be formed by a multi-step process, such as generally described in U.S. Pat. No. 7,811,553 at col. 8, line 60-col. 11, line 6. In short the two step process can include a first step of forming a poured soap base.

The poured soap base can be a tallow or vegetable-based soap base, a synthetic soap base, or a combination of these. In certain embodiments, the process of forming the soap base includes elevating the soap base ingredients to a temperature of no less than about 80° C. (e.g., no less than about 85° C., 90° C., 95° C., 100° C., or 105° C.). The soap base ingredients are in some embodiments subjected to these temperatures for a period of time no less than about 1 hour (e.g., no less than about 2, 3, 4, 5, 10, or no less than about 20 hours).

In a second step, a second phase is prepared, which can include one or more of the ingredients that are process-sensitive, such as certain pyrithione sources, the esters, the polyoxyethylene, fragrances, dyes, and other optional ingredients. The second phase can be prepared by warming glycerin to a temperature of from about 25° C. to about 50° C. (e.g., to about 35° C.) and adding any process-sensitive ingredients. The elevated temperature can aid in the incorporation of these ingredients, and can be selected on the basis of the particular ingredients that are being incorporated. For example, butters typically melt at about 35° C., so raising the temperature of the second phase to about 35° C. can aid in melting the butters into the phase. The selection of ingredients and amounts of the ingredients selected will vary, depending on the levels desired in the final shaving aid composition. In some embodiments, ingredients that are not themselves process-sensitive can be included in the second phase. The temperature of the second phase can in certain embodiments be maintained at from about 25° C. to about 50° C. (e.g., at about 35°) until such time as the second phase is added to the soap base. In other embodiments, the second phase can be allowed to cool (e.g., to room temperature) prior to being incorporated into the soap base.

As a third step, a shaving aid composition can be formed from the mixture of the soap phase and a second phase is illustrated in FIG. 1. A solidified poured soap base 202 is heated to a temperature of from about 90° C. to about 100° C. (e.g., to about 91° C., about 92° C., about 93° C., about 94° C., about 95° C., about 96° C., about 97° C., about 98° C., about 99° C., or about 100° C.) and remelted to form a melted soap 204. The melted soap 204 is metered via a pump 206 into a heated filler feed vessel 210 that is equipped with a stirring mechanism 212. Filler feed vessel 210 is configured to maintain the temperature of its contents at about 95° C. A second phase 220 is formed by intermixing the process-sensitive ingredients 224 in heated chamber 222. The second phase 220 is then metered via pump 228 into the filler feed vessel 210 and intermixed with the soap base 202 to form a molten shaving aid composition 230.

The molten shaving aid composition 230 is then metered via fill pumps 232 into individual molds 236 formed in a mold block 238, where the shaving aid composition is cooled to form molded shaving aid compositions 240. The temperature of the molten shaving aid composition 230 is maintained at a temperature of about 95° C. until the shaving aid composition is placed in the molds 236.

Because the molten shaving aid composition 230 can include process-sensitive ingredients 224, the molten shaving aid composition 230 is held at the elevated temperature for a period of time that is less than would result in substantial degradation of the process-sensitive ingredients 230. For example, in some embodiments, the molten shaving aid composition 230 is held at an elevated temperature for no more than about 120 minutes (including e.g., no more than about 110 minutes, no more than about 100 minutes, no more than about 90 minutes, no more than about 75 minutes, no more than about 60 minutes, no more than about 50 minutes, no more than about 40 minutes, no more than about 30 minutes, no more than about 20 minutes, no more than about 10 minutes, no more than about 5 minutes, or even no more than about 2 minutes) before it is placed into molds and cooled. In this fashion, a molded shaving aid composition can be formed in which the process sensitive ingredients are substantially non-degraded.

In certain embodiments, the shaving aid composition is placed into a mold having a shaving aid mounting device (e.g., the wings described below) already positioned in the mold. In this fashion, the shaving aid composition can embed itself into the shaving aid mounting device upon solidifying.

Once the shaving aid composition has cooled to a sufficient point (e.g., to the point that it has solidified enough to be easily separated from the mold), the shaving aid composition can be removed from the mold. In some embodiments, the shaving aid composition is allowed to cool to approximately room temperature before being removed from the mold. In other embodiments, the shaving aid composition is allowed to cool to a temperature no greater than about 80° C. (e.g., no greater than about 75° C., 70° C., 65° C., 60° C., 50° C., 40° C., no greater than about 30° C., no greater than about 25° C., no greater than about 20° C., no greater than about 15° C., no greater than about 10° C., no greater than about 5° C., or no greater than about 0° C.) before being removed from the mold.

One-Step Batch Process

In some embodiments, the pyrithione source and any process-sensitive ingredients can be added directly to the poured soap base melt in a one-step batch process. In one such embodiment, the poured soap base melt is maintained at about 95° C., and the second phase is added to the melt to form the shaving aid composition without first cooling and then re-melting the poured soap base melt. The shaving aid composition is then placed into one or more molds and cooled. In another such embodiment, the process sensitive ingredients are mixed directly into the poured soap base melt without first being incorporated into a process sensitive phase. The resulting shaving aid composition is then placed into one or more molds and cooled. In each case, the composition is placed in molds and allowed to cool before enough time has elapsed to substantially degrade some or all of the process sensitive ingredients. In particular, the time that elapses between adding the process-sensitive ingredients to the melted soap base and placing the molten shaving aid composition into the molds and cooling the shaving aid composition should be less than an amount of time in which some or all of the process-sensitive ingredients typically would begin to degrade at the elevated temperature and shear of the intermixing step. Generally, this time will be less than about 90 minutes (e.g., less than about 80, 70, 60, 50, 40, 30, 20, 10, or less than about 5 minutes).

Continuous Process

In some embodiments, the molded shaving aid composition is prepared in a continuous process. The ingredients for the soap base are first combined and flowed through a heated chamber to increase the temperature of the ingredients to at least about 90° C. (e.g., at least about 95° C., 100° C., 105° C., 110° C., 115° C., or at least about 120° C.). The heated chamber and pumping mechanism are configured to permit a sufficient dwell time of the soap base components at the elevated temperature to allow for sufficient melting and intermixing of the ingredients.

Next, the melt is moved into a second chamber maintained at no more than about 100° C. (e.g., no more than about 90° C., no more than about 80° C., or no more than about 70° C.). In the alternative, the melt can be retained in the first chamber, and the temperature of the first chamber can be reduced to no more than about 100° C. (e.g., no more than about 90° C., no more than about 80° C., or no more than about 70° C.). While maintaining this temperature, the process-sensitive ingredients are introduced and mixed into the soap base melt to form the shaving aid composition. The ingredients can be introduced individually, or can be introduced in the form of process sensitive phase, which is described above. The shaving aid composition is then flowed into a mold, e.g., by injection molding, and cooled to form a molded shaving aid composition.

Extruded Soap An extruded soap can be employed in certain embodiments. A process 250 for forming an extruded soap is illustrated in FIG. 1B. The soap base is generally formed by combining the soap base ingredients 252 in a reaction vessel 254 to form a liquid soap base 256 (e.g., by saponification or neutralization reaction) and glycerine 258, which is removed from the liquid soap base 256. The liquid soap base is moved to a drying chamber 260 where at least some of the water is removed (e.g., by vacuum spray drying) to form substantially dry soap pellets 262 (e.g., dry soap noodles or shavings). The dry soap pellets 262 are then introduced into an amalgamator 264 having one or more paddles 266 for mixing and/or grinding the dry soap pellets 266 along with process sensitive ingredients 270, which are introduced into the amalgamator 264, to form an extruded soap dry blend 272. The extruded soap dry blend 272 can in some embodiments be macromolecularly homogenized (e.g., a substantially even distribution of the process-sensitive ingredients among the dry soap pellets can be achieved). The extruded soap dry blend 272 is then refined, e.g., by introducing the extruded soap dry blend 272 into one or more rolling mills 274 to achieve a substantially uniform texture. The extruded soap dry blend 272 is then extruded using an extruder 276, optionally using heat (e.g., not more than 95° C., 90° C., 85° C., 80° C., 70° C., 60° C., 50° C., 40° C., 30° C., or not more than 25° C) and/or pressure, to form a continuous bar of extruded soap 278, which can be subjected to further processing steps 280 (e.g., cutting and/or stamping into the desired final shape).

IV. Other Ingredients in the Shaving Aid Composition

Wear Enhancers

The shaving aid composition includes one or more wear enhancing ingredients. Suitable wear enhancing ingredients include sodium stearate, polyoxyethylene, polyethylene, esters, and silicone polymers. Many of these ingredients (e.g., esters and polyoxyethylene) are typically process-sensitive. Wear enhancing materials can also impart other qualities or characteristics to the shaving aid composition, such as, e.g., increased lubrication.

Polyoxyethylene

One suitable wear enhancing ingredient is polyoxyethylene, which is a process-sensitive material. Polyoxyethylenes are typically characterized by their nominal, or average (number average), molecular weight. The number average molecular weight is the sum of individual molecular weights divided by the number of polymers. As is known in this field, a sample of polyoxyethylene generally includes a distribution of molecular weights such that the sample will include individual polymer molecules above and below the number average molecular weight.

Inclusion of a polyoxyethylene of any nominal molecular weight can improve the wear characteristics of the molded shaving aid composition. The polyoxyethylene can have an approximate nominal molecular weight of, for example, no less than about 100,000 daltons (e.g., no less than about 500,000, 1,000,000, 2,000,000, 3,000,000, 4,000,000, 5,000,000, 6,000,000, or no less than about 7,000,000 daltons) and/or no more than about 8,000,000 daltons (e.g., no more than about 7,000,000, 6,000,000, 5,000,000, 4,000,000, 3,000,000, 2,000,000, or no more than about 1,000,000 daltons). Optionally, two or more polyoxyethylenes having different nominal molecular weights can be employed. The polyoxyethylene can be present, for example, at a level of no less than about 0.1% (e.g., no less than about 0.25%, no less than about 0.5%, no less than about 1%, no less than about 2%, no less than about 3%, no less than about 4%, no less than about 5%, no less than about 6%, no less than about 7%, no less than about 8%, or no less than about 9%) and/or no more than about 10% (e.g., no more than about 9%, no more than about 8%, no more than about 7%, no more than about 6%, no more than about 5%, no more than about 4%, no more than about 3%, no more than about 2%, no more than about 1%, or no more than about 0.5%), based on the weight of the shaving aid composition. Exemplary polyoxyethylenes include members of the POLYOX® family of polyoxyethylenes, available from Union Carbide Corp, and ALKOX® polyoxyethylenes, available from Meisei Chemical Works, Kyoto, Japan.

Silicone Polymers

Silicone polymers can also be employed as a wear enhancing ingredient. In particular, silicone cross-polymers may be used. Silicone cross-polymers are polymers including silicone (e.g., having a silicone-based backbone) that are capable of cross-linking (e.g., that are cross-linked). Silicone polymers, particularly silicone cross-polymers, can be present at levels of at least about 0.25% active in a solvent (e.g., at least about 0.5%, 1%, 1.5%, 2%, 2.5%, 3%, 3.5%, 4%, or at least about 4.5%) and/or at most about 5% (e.g., at most about 4.5%, 4%, 3.5%, 3%, 2.5%, 2%, 1.5%, 1%, or at most about 0.5%). In certain embodiments, the silicone cross-polymer will be present at levels of from about 0.25% to about 5%. Exemplary silicone cross-polymers include, for example, lauryl dimethicone/polyglycerin-3 cross-polymer (e.g., 30% lauryl dimethicone/polyglycerin-3 cross-polymer). Commercially available silicone cross-polymers are known and are disclosed in U.S. Pat. No. 7,811,553 at col. 6.

Esters

Esters (for example, butters and other non-liquid esters) can be incorporated into the shaving aid composition, and can function as a wear enhancer and/or as a skin-softener. In particular, semi-solid esters may be employed and they are generally process-sensitive materials. The semi-solid esters can act as an emollient and/or as a moisturizer. Exemplary semi-solid esters include butters such as, for example, shea butter, cocoa butter, kokum butter, avocado butter, olive butter, mango butter, and mixtures thereof. Esters can be incorporated into the shaving aid composition in levels of no less than about 0.5% (e.g., no less than about 1%, 2%, 3%, 4%, 5%, 6%, or no less than about 7%) and/or no more than about 8% (e.g., no more than about 7%, 6%, 5%, 4%, 3%, 2%, or no more than about 1%).

Polyethylene Compositions

The shaving aid composition can include one or more polyethylene compositions as wear enhancing ingredients. Generally, polyethylenes can improve the wear characteristics of the shaving aid composition, but are difficult to incorporate into the composition directly. Instead, the polyethylenes can be incorporated into a composition that is then incorporated into the shaving aid composition. For example, a composition including polyethylene, polybutene, and mineral oil (for example, sold under the trade name Covagloss by Sensient Technologies) can be employed. In some embodiments, the shaving aid composition will include no less than about 0.5% (e.g., no less than about 1%, 2%, 3%, 4%, 5%, 6%, or no less than about 7%) and/or no more than about 8% (e.g., no more than about 7%, 6%, 5%, 4%, 3%, 2%, or no more than about 1%) of a polyethylene, polybutene, and mineral oil composition.

Moisturizer Components and Other Optional Ingredients

The shaving aid composition can further include other skin care ingredients and/or other additives. Skin care ingredients that may be added to the base to enhance the composition include, but are not limited to, surfactants (e.g., sodium isostearoyl lactylate, ammonium isostearate, DEA-myristate, alkyl glyceryl sulfonate, and laureth-16), skin care agents such as petrolatum (e.g., emollients, lubricants, humectants, moisturizing agents, and conditioners), foaming agents, hair growth inhibitors, botanical extracts, antioxidants, antimicrobials, anti-inflammatory agents, astringents, anti-irritants, depilatory agents, medicinal agents, absorbants, fragrances, coloring agents (e.g., dyes and pigments) and exfoliating agents (e.g., loofa, seaweed, oatmeal, pumice, apricot seed, and the like). Exemplary embodiments of skin care agents include, but are not limited to, humectants such as glycerin, sorbitol, and propylene glycol, skin freshening and soothing agents such as menthol, aloe, allantoin and collagen, lubricants such as polyoxyethylene, and silicones (e.g. dimethicone, dimethiconol, dimethicone copolyol, stearyl dimethicone, cetyl dimethicone copolyol, phenyl dimethicone, cyclomethicone, etc.), sodium or potassium salts (e.g., lactylates, chlorides, sulfonates, and the like), vitamins and vitamin complexes (including vitamin precursors and derivatives), cocoates, metal oxides, oils (e.g., cocoa butter), dimethicone, allantoin, sucrose cocoate, oleyl lanolate, thiourea, tocopheryl acetate, PPG-33, undeceth-3, honey, algae and aloe barbadensis. The skin care ingredients can in some embodiments be present in amount of no more than about 35% (e.g., no more than about 30%, 25%, 20%, 15%, 12%, 10%, 8%, 6%, 4%, or no more than about 2%). The absorbents can be clays or clay-based compositions, kaolin, wood powder, sodium chloride, cyclodextrin, chalks, talcs, silicas, polytetrafluoroethylene, or the like, and can be present in amounts of no more than about 9% (e.g., no more than about 5% or no more than about 3%). Clays that may be added include bentonite, kaolin, combinations of the foregoing clays, and the like. Exemplary coloring agents include dyes and pigments, for example, titanium dioxide, manganese violet, zinc oxide, an Ultramarine (e.g., Ultramarine Blue 4), Orange 4, Green 3, or other dyes or pigments approved for use in cosmetics, either alone or in combination. Coloring agents can in certain embodiments be added in an amount of no more than about 6% (e.g., no more than about 4%, 2%, 1%, 0.1%, 0.01%, 0.001%, 0.0001%, or even no more than about 0.00001%) and/or no less than about 0.000001% (e.g., no less than about 0.00001%, 0.0001%, 0.001%, 0.01%, 0.1%, or no less than about 1%) by weight.

Fragrances are odorants used to impart desirable smells to the composition and may further mask the less desirable odors of other components of the composition. Any fragrance approved for use in cosmetics may be employed. In certain embodiments, at least one fragrance ingredient can be added in an amount up to about 4% (e.g., up to about 2%, up to about 1.5% or up to about 1%).

An exemplary process sensitive phase includes the following:

| | |
|---|---|
| Glycerin | 62.4% |
| Shea butter | 5.4% |
| Fragrance (IFF 4473-BH) | 5.4% |
| POLYOX ® WSR coagulant (MW approximately 5 million) | 26.9% |
| D&C Red 33 Dye | 0.005% |

Wear Characteristics of the Shaving Aid

In some embodiments, the shaving aid composition exhibits good wear characteristics. Wear characteristics can be determined in a number of ways. For example, the shaving aid composition can be incorporated onto a razor, and the number of shaves before certain shaving performance characteristics begin to degrade can be determined. In other embodiments, the wear can be determined by subjecting the shaving aid composition to set abrasive conditions (e.g., a given surface composition and speed of an abrasive device such as, e.g., an abrasive wheel) and determining how much of the composition wears off in a given time period.

In some embodiments, wear resistance can be measured by maintaining a flow of water over a textured surface and between this textured surface and the shaving aid body. This process is described in U.S. Pat. No. 7,811,553 at col. 12, lines 33-56. Another wear test utilizes cartridges of shaving aid composition molded to a holder and testing the cartridge using a wet wheel apparatus. This process is described in U.S. Pat. No. 7,811,553 at col. 12, line 57-col. 13, line 13.

V. Razor Details

Razors Including a Molded Shaving Aid Composition

Figure 2A:
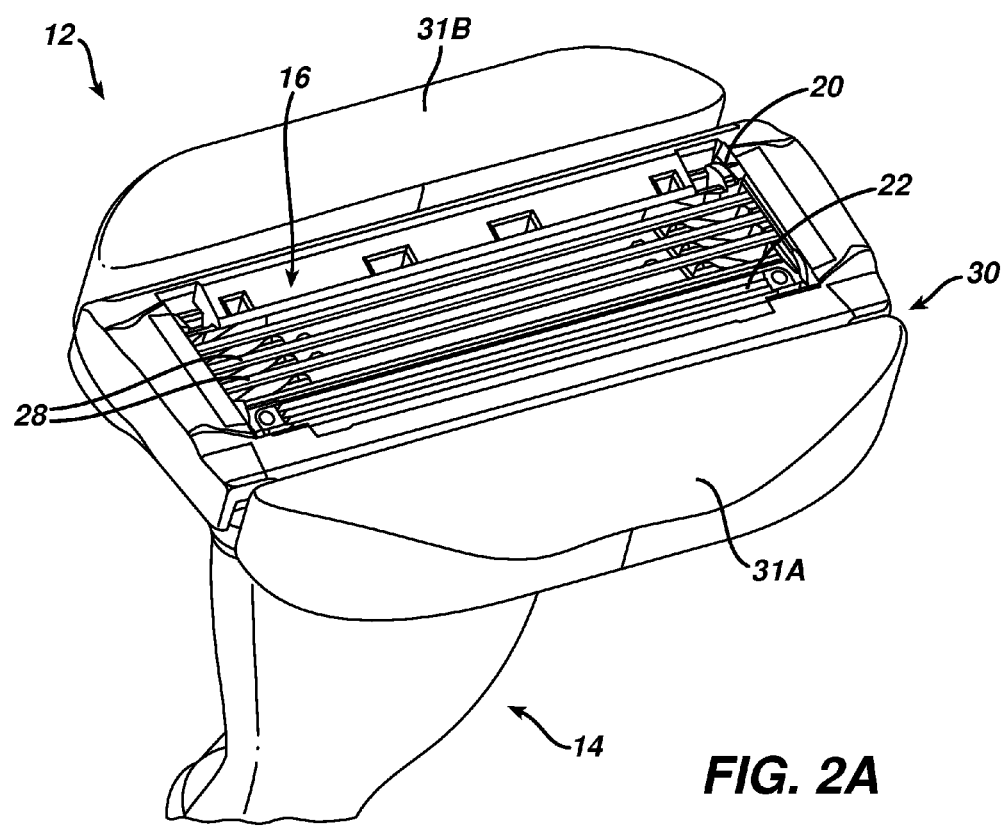
FIG. 2A is a perspective view of the head and neck portion of a razor according to one embodiment of the invention.
Figure 2B:
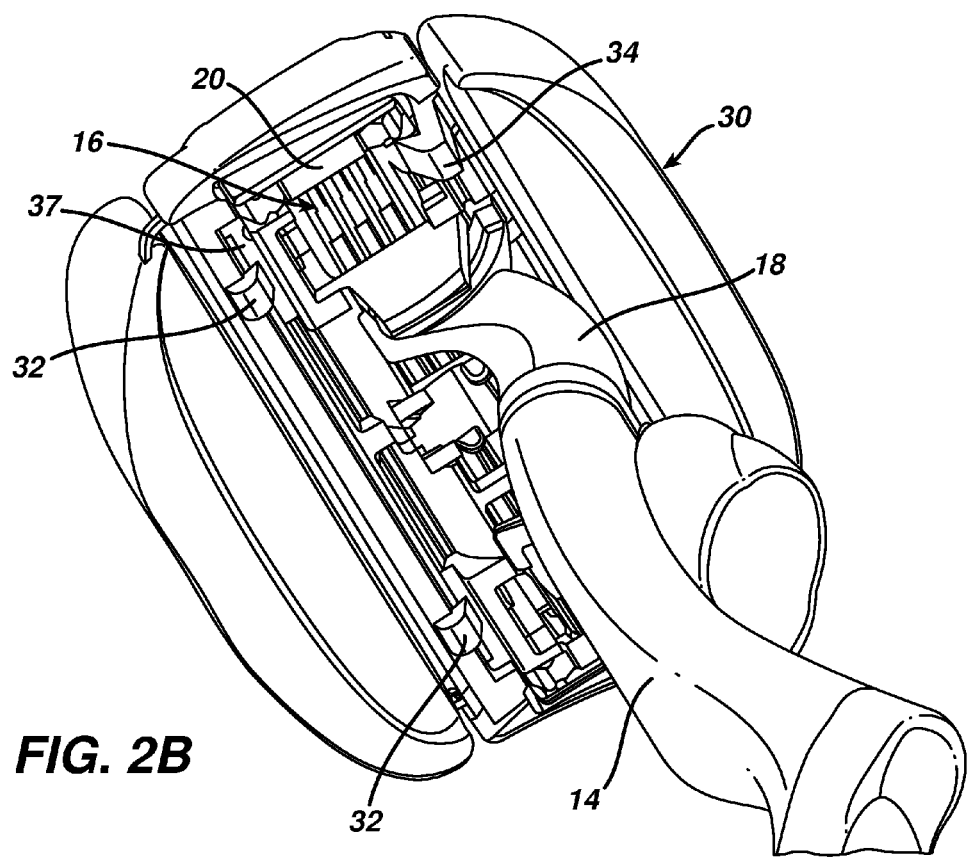
FIG. 2B is a perspective view of the head and neck portion shown in FIG. 1, viewed from the back.

The molded shaving aid compositions are in certain embodiments incorporated into a razor, e.g., into a razor head. For example, the molded shaving aid composition can be attached to one or more holders, which are themselves configured to be attachable to a razor head. Referring to FIGS. 2A, 2B, and 3, a shaving razor 10 includes a disposable cartridge 12 and a handle 14. As shown in FIG. 3, cartridge 12 includes a connecting member 18, which removably connects cartridge 12 to a connecting portion 19 of handle 14, a blade unit 16, which is pivotally connected to connecting member 18, and a shaving aid holder 30 mounted on the blade unit 16. Referring to FIG. 2A, the blade unit 16 includes a plastic housing 20, a guard 22 at the front of housing 20, and blades 28 between guard 22 and the rear of housing 20. The blade unit 16 can be similar to blade units described in U.S. Pat. No. 5,661,907.

The handle 14 can be similar to those described in U.S. Pat. Nos. 5,855,071, 5,956,851 and/or 6,052,903. The connecting member 18 that is used to connect blade unit 16 to handle 14 can be similar to connecting members described in U.S. Patent Publ. Nos. 2006/0080837A, titled "Shaving Razors and Cartridges," filed on Oct. 20, 2004, and 2006/0080838A, and/or U.S. Pat. No. 8,033,023.

As will be discussed in further detail below, the holder 30 carries a pair of shaving aid portions 31A, 31B. The front shaving aid portion 31A contacts the skin in front of the blades, i.e., before shaving, and the rear shaving aid portion 31B contacts the skin behind the blades. One or both of the shaving aid portions are formed of the molded shaving aid composition described herein, while one of the shaving aid portions can optionally include a different or additional composition. For example the front shaving aid portion may include the molded shaving aid composition, while the rear portion may include skin soothing and conditioning ingredients such as emollients and moisturizers in place of or in addition to the shaving aid portion.

Figure 4B:
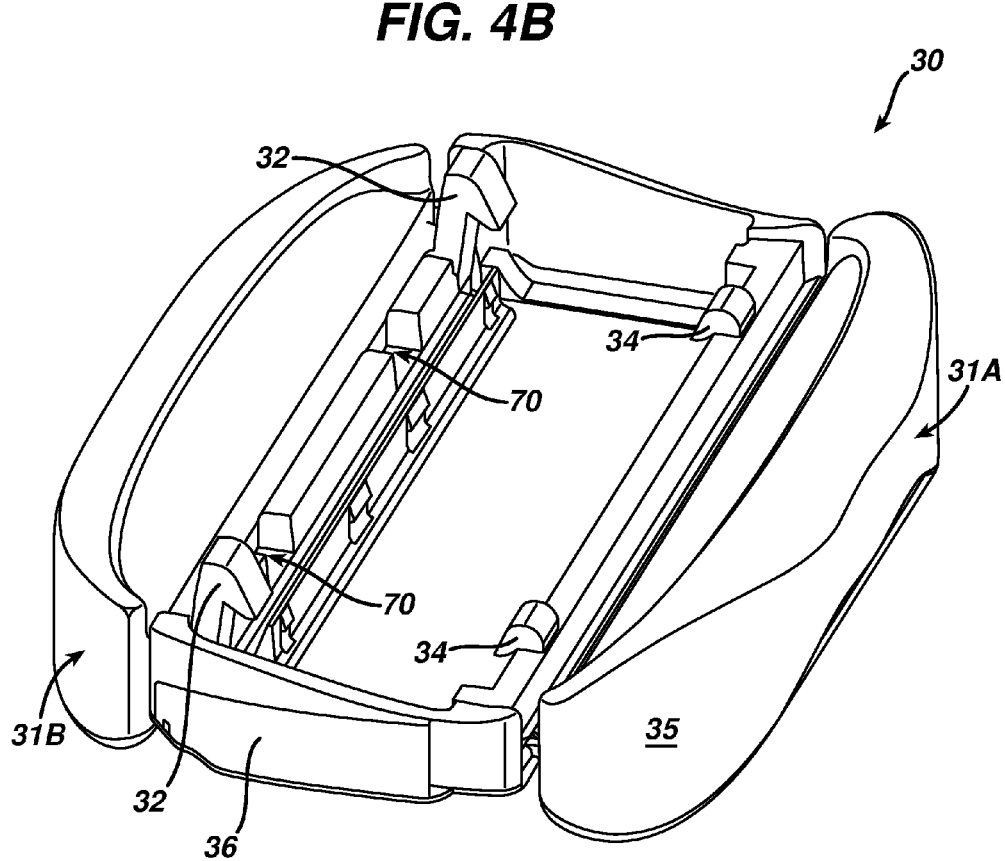
FIG. 4B is a perspective view of the holder shown in FIG. 3, viewed from below.
Figure 4C:
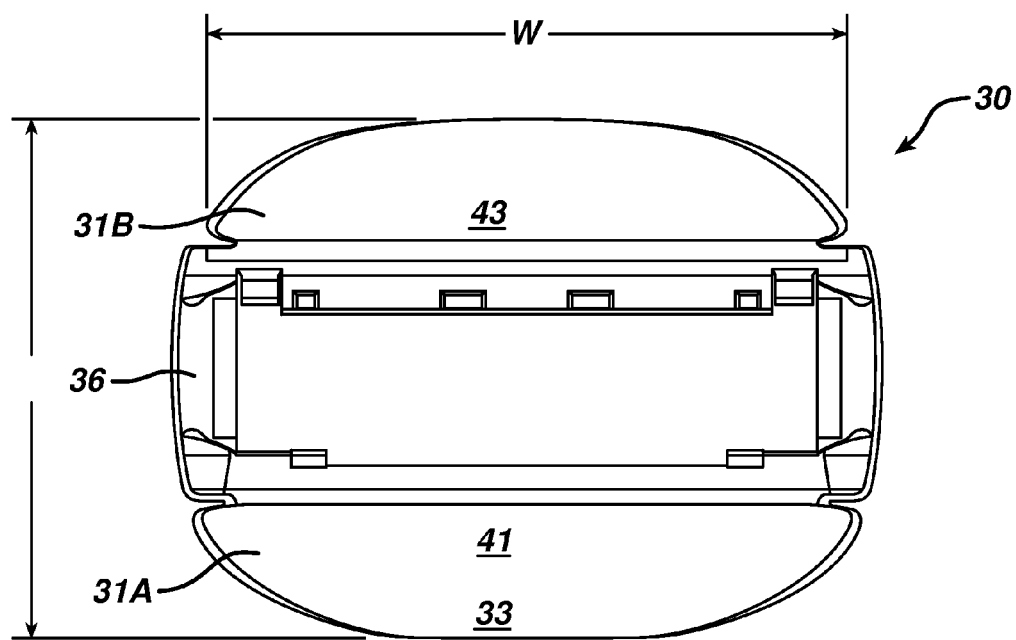
FIGS. 4C, 4D and 4E are, respectively, top, front, and side views of the holder shown in FIG. 3.
Figure 4D:
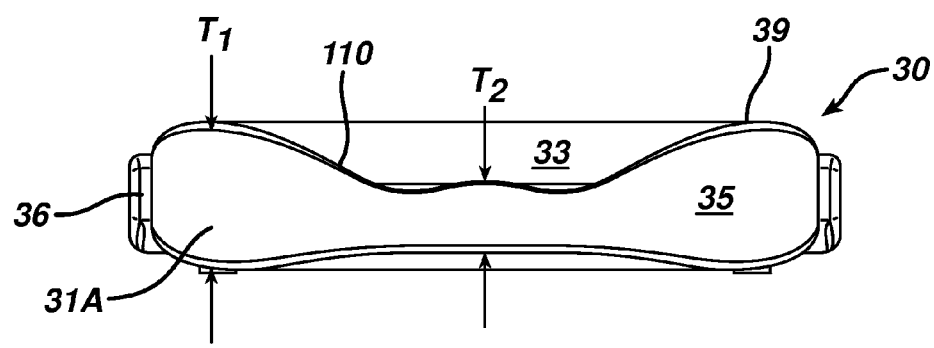
Figure 4E:
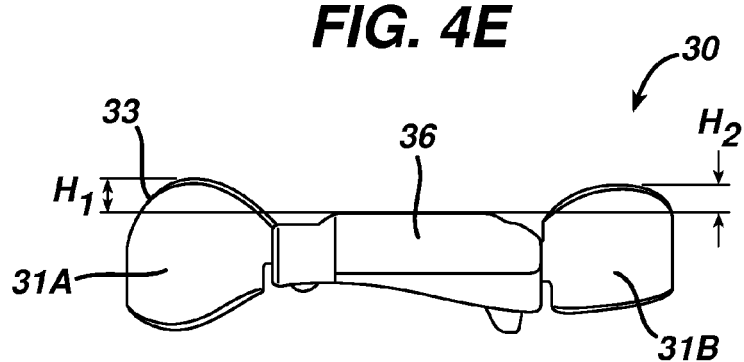
Figure 4F:
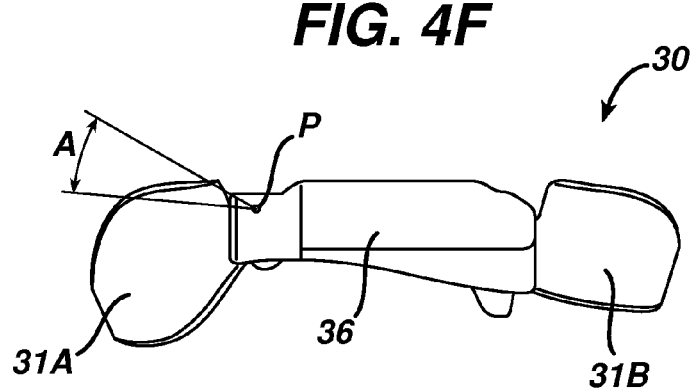
FIG. 4F is a side view showing the wings of the holder in a deflected position (the side mounts are shown in their normal position in FIG. 3D).
Figure 5A:
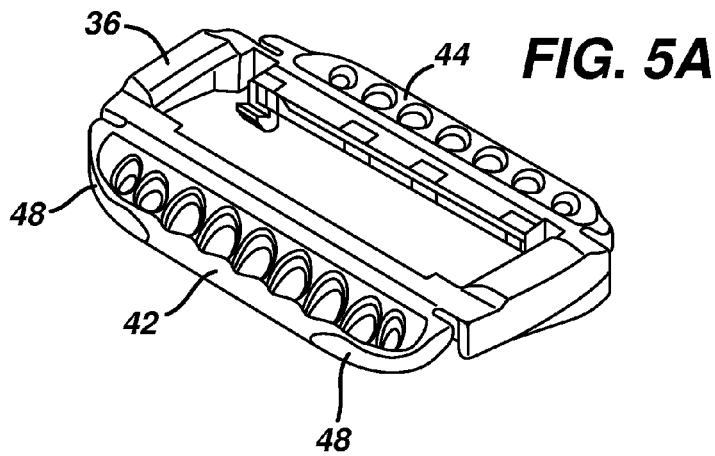
FIGS. 5A, 5B, 5C, and 5D are, respectively, perspective, top, front and side views of the holder with the shaving aid portions removed.
Figure 5B:
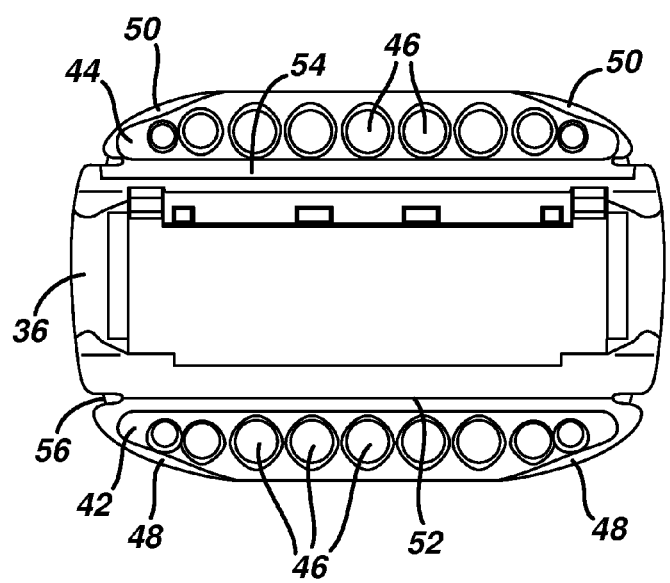
Figure 5D:
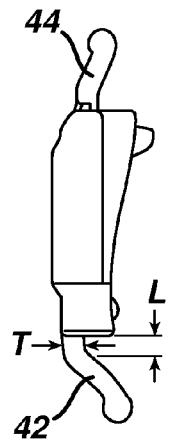
Figure 5C:
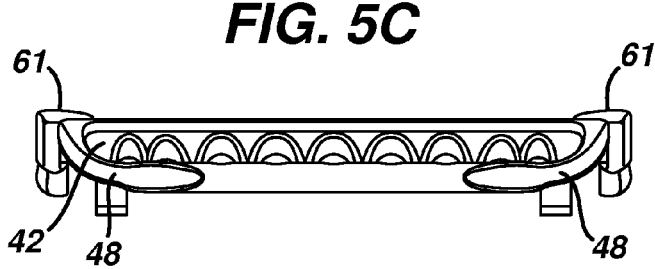

The shaving aid portions are mounted so that they will resiliently deflect upon contact with the skin, from a normal, undeflected position (FIG. 4E) to a flexed position (FIG. 4F). This deflection allows the razor to be easily used in hard to reach or confined areas, such as the armpit (axilla) or behind the knee. Deflection of the shaving aid portion also prevents premature wear of the shaving aid portion and discomfort to the user in cases where the user applies excessive pressure during shaving. Preferably, the angle of deflection (angle A, FIG. 4F) is at least about 10 degrees, e.g., from about 10 to 60 degrees, typically about 20 to 40 degrees. Angle A is measured by drawing a line from a pivot point P located in the approximate center of the elastomeric hinge to the highest point on the shaving aid portion 31A when the shaving aid portion is in its undeflected position, and measuring the angle between this line when the shaving aid portion is in its undeflected position and the same line when the shaving aid portion is deflected to its design limit. The resilient mounting of the shaving aid portions will be discussed in further detail below. The heights H1 and H2 of the shaving aid portions in the undeflected position (FIG. 4E) will vary, but may be, for example, from about 1 to 4 mm, e.g., about 1.5 to 3.0 mm H1 and H2 are generally within about 0 to 50% of each other. Generally, the heights of the two shaving aid portions will be proportional to the wear rates of the compositions used, so that the shaving aid portions will be exhausted at approximately the same time.

The holder 30 may be mounted so that it is removable from the cartridge body by the consumer (e.g., if the consumer wishes to add a shaving aid holder to a cartridge that does not include one), or, alternatively, may be permanently mounted on the cartridge body or integrally molded with the cartridge body. In the embodiment shown in FIGS. 2A-6D, the holder 30 clips onto the cartridge by engagement of clips 32 and 34 (FIG. 4B) with the back surface 37 of the housing 20 of the blade unit, as shown in FIG. 2B. The holder 30 may be engaged with the housing by sliding the housing under clips 34 and then deflecting clips 32 to snap them in place.

Structure of the Shaving Aid Holder

Referring to FIG. 4A, shaving aid holder 30 includes a frame member 36 that extends around the periphery of the cartridge body when the holder 30 is in place. Generally, frame member 36 is formed of a molded plastic. In some embodiments, the sides 38 of the frame member extend over side regions of the cartridge body, to securely hold the holder in place. Sides 38 should generally be sufficiently thin, adjacent the blade ends, so that shaving performance is not compromised. In some embodiments, a ramped area is provided between the very thin edges 40 adjacent the blade ends to an area outboard of the edges. For example, the sides 38 generally have a thickness of less than 0.15 mm at edges 40, and less than 0.4 mm at line L, about 0.5 mm inboard of edges 40. This ramped area 59 provides rails 61, between line L and the outer side edge 63 of the holder 30, that may enhance tracking of the razor during use.

Referring to FIGS. 4E, 5A-5D and 6A-6D, shaving aid portions 31A and 31B are carried on a pair of wings 42, 44. Wings 42, 44 may be formed of the same plastic as the frame, or may be formed of a different material. For example, the wings may be formed of the same material as the hinges 52, 54 (FIG. 5B, discussed below) that join the wings and frame.

In this case, the wings and hinges may be overmolded onto the frame in a single molding step.

The wings include a plurality of apertures 46 (FIG. 5B) that allow the shaving aid to flow through the thickness of the wing and form a mechanical interlock (e.g., by flowing together to form a unitary mass) on the back side of the wing, securing the shaving aid to the wing.

Elastomeric bumpers 48, 50 are provided at the corners of the wings, underlying the shaving aid portions, so that as the shaving aid portions are exhausted the user's skin will contact elastomer rather than hard plastic. Generally, the elastomeric bumpers have a thickness T (FIG. 6C) of at least 1 mm, e.g., about 1.5 to 3 mm. In some embodiments, the elastomer is relatively soft for user comfort and so that the hinge will have a soft flex. For example, the elastomer may have a hardness of less than about 50 Shore A, e.g., less than about 40 Shore A. The elastomer may be, for example, a block copolymer such as those available under the tradename KRATON®. In some embodiments, the elastomer has sufficient chemical resistance so that it will not degrade during prolonged contact with the ingredients of the shaving aid composition.

Figure 6D:
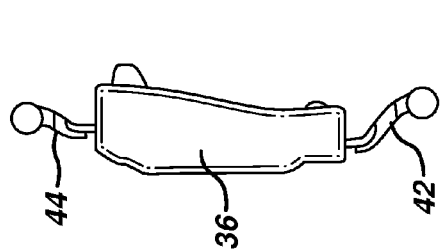
FIGS. 6A, 6B, 6C, and 6D are, respectively, perspective, top, front and side views of the holder with the shaving aid portions and elastomeric portions removed.
Figure 6A:
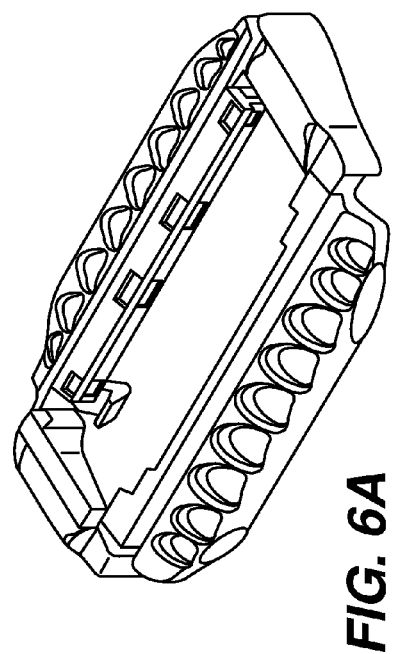

Referring to FIG. 6D, even in their normal, undeflected position, the wings 42, 44 curve downward, well below the plane defined by the blade edges. This curvature allows the wings to carry a relatively large amount of soap, without the upper surface of the shaving aid portion extending too far above the plane of the blade edges or the lowest area of the shaving aid portion being too low to ever contact the skin during use. Generally, the lowest point on each of the wings 42, 44 is at least about 1 mm below the plane defined by the blade edges, e.g., about 2 to 6 mm below this plane. If desired, e.g., if the shaving aid is relatively wear resistant, the wings may extend relatively straight from the frame. In one embodiment, the shaving aid and shaving aid holder can be similar to that used on the Venus Breeze® line of 2-in-1 razor, and/or the Schick® Intuition® line of razors. In another embodiment, the shaving aid and shaving aid holder can be similar to those disclosed U.S. Patent Publ. Nos. 2006/225285A and 2006/080837A, and/or U.S. Pat. No. 7,811,553.

Resilient Mounting of Shaving Aid Portions

Wings 42, 44 are resiliently mounted on the frame member 36, to allow deflection of the shaving aid portions 31A, 31B during shaving, from the normal position shown in FIG. 4E to the deflected position shown in FIG. 4F. Flexible hinges 52, 54 (FIG. 5B) provide this resilient connection between the wings and the frame.

In some embodiments, hinges 52, 54 are formed of an elastomeric material, e.g., a block copolymer. Typically, the hinges are formed of the same elastomeric material as the elastomeric bumpers 48, 50 discussed above. The elastomeric material is generally selected to provide a soft flex, so that the wings deflect readily upon contact with the user's skin, while also providing a good spring return to the wings. For example, the elastomeric material may have a flexural modulus of about 100 to 300 psi. The modulus that will provide the desired product characteristics will depend upon the thickness T and length L (FIG. 5D) of the hinges. The thickness and length of the two hinges can be the same or different, and these dimensions and the elastomeric material used can be selected to give the two wings desired flexural characteristics. The thickness of the hinges may be, for example, from about 0.5 to 2.0 mm and the length may be from about 0.5 to 3.0 mm. In the embodiment shown in FIGS. 5A-5D, the hinges extend almost the full width of the holder 30. However, if desired, the hinges may be narrower or may consist of discontinuous hinge portions.

Figure 6B:
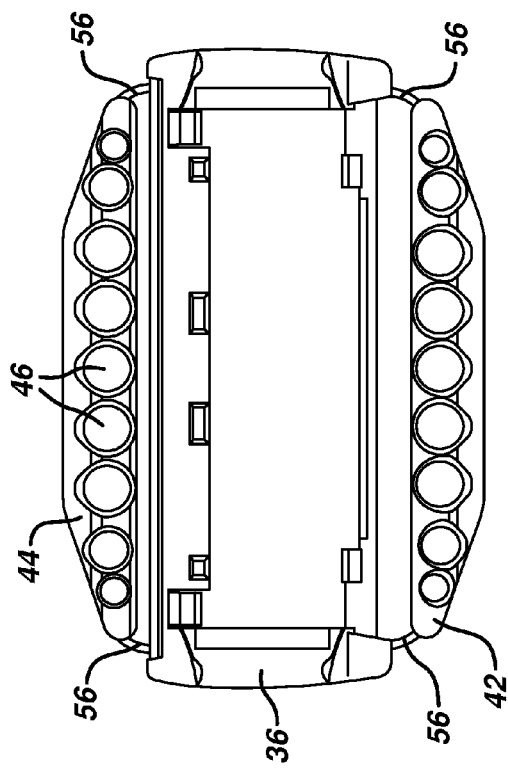
Figure 6C:
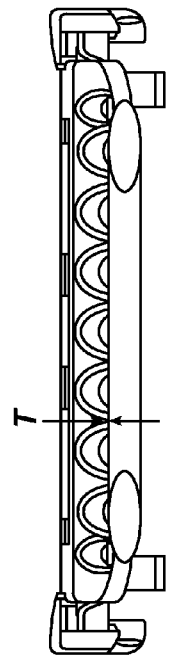

The elastomeric hinges may be overmolded onto the frame. To assist in this process, in the embodiment shown in FIGS. 5A-6D, the frame is connected to each of the wings by a pair of connecting members 56 that extend integrally from the frame to the wings (FIG. 6B). If desired, these connecting members may be cut after overmolding has been completed. Alternatively, the wings and frame may be separate components that are placed in an insert mold and overmolded with elastomer. Forming the hinges solely of elastomer (i.e., substantially free of rigid plastic) may result in a softer flexing hinge in some cases. The shaving aid portions can also be attached to the frame as described in U.S. Patent Publication No. 2011/0247216A, titled "Shaving Cartridge Having Mostly Elastomeric Wings", filed on Mar. 8, 2011.

Contouring of Shaving Aid Portions

Referring to FIG. 4E, the front shaving aid portion 31A includes a ramped leading surface 33 that is contoured to cause the shaving aid portion to deflect upon skin contact, so that the cartridge will not rock back when shaving aid portion 31A contacts the skin during shaving. As can be seen in FIGS. 4A and 4D, a leading edge 110 of the shaving aid portion 31A has a first thickness t1 adjacent the side surfaces of the holder 30, and tapers to a second, lesser thickness t2 adjacent a center region of the shaving aid portion. This shape allows the front shaving aid portion to have the ramped leading surface 33, while still providing as much shaving aid as possible adjacent the side surfaces. If desired, the entire leading edge could have the lesser thickness t2. The front face 35 of the shaving aid portion 31A includes smoothly curved, arcuate side areas 37A, 37B, to enhance the soap-deflecting contour of leading surface 33 and to avoid edges and corners that could be uncomfortable during shaving and facilitate shaving of tight areas such as the underarm and behind the knee. Similarly, the intersections 39 of leading surface 33 and front face 35 are smoothly radiused.

Both the front shaving aid portion 31A and the rear shaving aid portion 31B are contoured so that the upper surface of each shaving aid portion (surface 41 of shaving aid portion 31A and surface 43 of shaving aid portion 31B) lies relatively flat against the user's skin when the wing 44 is deflected. This flat position, shown in FIG. 4F, allows as much shaving aid as possible to be in contact with the user's skin during shaving.

Ease of Shaving

Shaving aid portions 31A, 31B have a width W at their widest point (FIG. 4C) that is equal to or slightly less than the width of the frame 36 of the holder 30. Thus, the shaving aid portions do not extend beyond the side walls of the frame 36. As a result, the area around the side walls of the frame is unobstructed, allowing the shaver to determine, by sight and/or tactile sensation, what area has been shaved. If desired, the shaving aid portions may extend slightly beyond the side walls of the frame, e.g., by 2 mm or less on each side.

Shaving is also facilitated by rails 61 (FIGS. 4A, 5C), discussed above, which can engage the user's skin during shaving, potentially enhancing tracking of the cartridge.

While the embodiments described above have a pair of shaving aid portions, the razors can in the alternative have a single shaving aid portion, which can be located in front of the blades, behind the blades, or can extend completely around the blades.

VI. Characteristics

ZPT Particle Size Test Method

ZPT particle size can be measured by conventional light scattering means, such as a Horiba LA-910 particle size analyzer with flow cell. More specifically, disperse a ZPT suspension in water to the target optical density, about 90% and measure the particle sizes with, for example, the Horiba LA-910 particle size analyzer, which uses spherical assumptions for all calculations and calculates the particle size and other parameters based on volume distribution. A relative refractive index of 1.28 with no imaginary portion is used for the calculations and agitation set on 2. The span is a unitless parameter calculated as the breadth of the distribution as [D90-D10]/D50 using the mean diameters at 90%, 10% and 50% of the distribution.

Deposition Test Method

To determine the amount of ZPT deposited on a substrate, perform a cup scrub procedure. To perform the cup scrub procedure, apply an extraction solvent or solution such as an extraction solvent comprised of 80% 0.05M EDTA and 20% ethanol to a substrate surface such as the 2×2.5 cm rectangular pieces of pigskin discussed above to solubilize and remove the ZPT (platelet and particulate). For example, place a 2 cm diameter glass cup that includes 1 ml of extraction solution on the substrate surface. Agitate or rub the substrate area circumscribed by the glass cup and in contact with the extraction solution with a glace policeman for 30 seconds. After agitation or rubbing, remove the extraction solution from the glass cup via a transfer pipette and place the first aliquot of extraction solution in an amber glass vial. Repeat the procedure, e.g., place a 2 cm diameter glass cup that includes 1 ml a second aliquot of extraction solution, agitate or rub as indicated above, and remove the second aliquot solution from the glass cup via a transfer pipette. Then, add the second aliquot of extraction solution to the amber glass vial that includes the first aliquot of extraction solution (a total of 2 ml of extraction solution per extracted area). Then, analyze the extraction solution (combined first and second aliquots) using a HPLC-UV measurement such that a measure of ZPT per unit volume of extraction solution can be yielded. Next, calculate ZPT per deposited per unit area based on the ZPT per unit volume and the surface area of the extracted region of the substrate surface.

Water Activity Test Method

Water Activity ("Aw") is a measurement of the energy status of the water in a composition. Water activity ("Aw") is defined as the ratio of the water vapor pressure over a sample (P) to pure water vapor pressure at the same temperature (P0), expressed fractionally:

$$Aw = P/P0$$

Water activity is measured by a number of conventional, automated techniques including but not limited to the chilled-mirror dewpoint, and capacitance of the equilibrium headspace over a composition. At equilibrium, the relative humidity of the air in the chamber is the same as the water activity of the sample.

For purposes of the present invention, the Aw of a bar composition can be measured using the AquaLab Series 3 Water Activity Meter available from Decagon Devices, Inc. of Pullman, Wash. USA. The Water Activity is measured at 25° C. utilizing the following procedure:

1. Check the sample container of the meter to make sure it is clean and dry before the test;
2. Cut a soap base composition into 0.2 to 0.4 cm thick pieces with stainless knife;
3. Put pieces into the container of the meter to a ⅓" to ½" depth;
4. Press the composition with a gloved finger lightly to make sure the bottom of the container is covered;
5. Put the sample container back into the sample cabinet of the meter and cover it, and turn dial to activate the meter;
6. Wait for the equilibrium until a green LED flashing and/or beeps; and
7. Record the test temperature and Aw.

Discoloration Test Method

One method of quantitatively measuring discoloration inhibition efficacy is described. First, the soap is dissolved in water to reach a 10% solution following the process described above for soap solution preparation for pH measurement. Then the ferrate is added into the soap solution to reach a total iron concentration of 20 ppm based on the weight of the solution. Then the color (L value) of the soap solution before and after adding ferrate is measured to get a delta L by deducting the value measured before adding from the value after adding. Here, "L" stands for brightness or whiteness of the sample measured. The absolute value of delta L divided by the original L value measured before adding ferrate is expressed as a percentage. When the percentage is less than 7%, preferably less than 5%, 3%, 1%, 0.5%, the sample bar can be considered as having decreased discoloration problem. A spectrophotometer (e.g., Macbeth COLOR-EYE 3100 spectrophotometer from Gretagmacbeth) can be used to measure the L value.

Another method of showing the discoloration inhibition efficacy is an iron nail piercing test. This test mimics the real life situation where the bar soap comprising a pyrithione source has a chance of contacting metallic surfaces during manufacturing and/or during consumer use in a high moisture environment, thereby causing a discoloration problem. In the piercing test, a bar soap which has been pierced with and now containing an embedded iron source, is soaked completely under water for 30 minutes at room temperature. Then, the water is removed and let the bar stand for 24 hours at room temperature. Then, the iron nails are removed then and the bar soap surface is checked for discoloration at the area where the iron nail contacts the bar.

VII. EXAMPLES

The invention is further described in the following examples, which do not limit the scope of the invention described in the claims.

Soap Base Comprising a Pyrithione Source

An experimental soap base in the form of soap noodles is made in accordance with the present invention. This experimental soap base can be used with one or more of the examples of U.S. Pat. No. 7,811,553 in place of the soap base disclosed in said reference. Soap Noodles are made via a conventional process involving a crutching step and a vacuum drying step. The Soap Noodles are then added to an amalgamator. The ingredients of water and platelet ZPT are added to the amalgamator and then mixed for about 30 to 45 seconds. This soap mixture is then processed through conventional milling, plodding, and stamping steps to yield finished bar compositions. According to example embodiments, the finished bar composition can be similar to exiting soap bases or may be slightly smaller (e.g. can have dimensions half of a typical soap base). For example, the finished bar composition can be sized to form a shaving aid composition.

| Ingredient | Ex. 1 | Ex. 2 | Ex. 3 | Ex. 4 |
|---|---|---|---|---|
| Soap Noodle [a] | 98.38% | 97.78% | 97.38% | 95.38% |
| Platelet ZPT [b] | 0.25% | 0.4% | 0.5% | 1.0% |
| Brightener-49 | 0.02% | 0.02% | 0.02% | 0.02% |
| TiO$_2$ | 0.50% | 0.50% | 0.50% | 0.50% |
| Perfume | 1.10% | 1.10% | 1.10% | 1.10% |

-continued

| Ingredient | Ex. 1 | Ex. 2 | Ex. 3 | Ex. 4 |
|---|---|---|---|---|
| Water | QS | QS | QS | QS |
| Moisture Loss | −1.00% | −1.00% | −1.00% | −1.00% | a The Soap Noodle utilized in these examples has the following approximate composition: about 67.2% Tallow Soap, about 16.8% Coconut Soap, about 2% Glycerin and about 14% water. These percentage amounts are by weight of the Soap Noodle.
b U2 Zinc Pyrithione, added from 25% active suspension, Arch Chemicals, Inc., Norwalk, Connecticut, USA
c Fine Particle Size Zinc Pyrithione, added from 48% active suspension, Arch Chemicals, Inc.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All measurements are performed at 25° C., unless otherwise specified.

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern. Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shaving cartridge comprising:
a housing having a front edge and a rear edge;
one or more shaving blades between the front edge and the rear edge;
a shaving aid holder; and
at least one shaving aid portion mounted on the shaving aid holder, the shaving aid portion comprising from about 0.1% to about 10 wt % polyoxyethylene, a pyrithione source, and a soap base,
wherein said soap base comprises a pH adjusting agent selected from a group consisting of ammonia solution, triethanolamine, diethanolamine, monoethanolamine, potassium hydroxide, sodium hydroxide, soluble carbonate salts, and combinations thereof, wherein said soap attains a pH of greater than or equal to 10.7, and wherein said pH adjusting agent is present in an amount of from about 0.3% to about 20% by weight of the soap base.

2. The shaving cartridge of claim 1, wherein said pyrithione source is at a level of from about 0.01% to about 5%, by weight of the soap base.

3. The shaving cartridge of claim 1, wherein the pyrithione source is selected from a group consisting of zinc pyrithione, sodium pyrithione, pyrithione acid, dipyrithione, chitonsan pyrithione, magnesium disulfide pyrithione, and combinations thereof.

4. The shaving cartridge of claim 1, wherein said pyrithione source is in the form of a platelet having a mean particle diameter of about 0.5 microns to about 10 microns, a median particle diameter of about 0.5 microns to about 10 microns, and a thickness of about 0.6 microns to about 15 microns.

5. The shaving cartridge of claim 4, wherein the mean particle diameter is about 1 microns to about 5 microns.

6. The shaving cartridge of claim 4, wherein the median particle diameter is about 0.6 microns to about 0.7 microns.

7. The shaving cartridge of claim 4, wherein said soap base comprises from about 0.1% to about 1.0%, by weight of the soap base, of the pyrithione source.

8. The shaving cartridge of claim 4, wherein the platelet comprises a span of about 5 or less.

9. The shaving cartridge of claim 1, wherein said soap base further comprises an additional antibacterial agent selected from the group consisting of triclocarban; triclosan; a halogenated diphenylether; hexachlorophene; 3,4,5-tribromosalicylanilide; salts of 2-pyridinethiol-1-oxide; and mixtures thereof.

10. The shaving cartridge of claim 1, wherein said soluble carbonate salt is selected from a group consisting of sodium carbonate, potassium carbonate, ammonium carbonate, aluminum carbonate, magnesium carbonate, sodium bicarbonate, potassium bicarbonate, and combinations thereof.

11. The shaving cartridge of claim 1, further comprising a zinc source selected from the group consisting of an organic carboxylic zinc salt, an inorganic zinc salt, zinc hydroxide, zinc oxide, and combinations thereof, wherein the zinc source is in present in an amount of from about 0.01% to about 0.5%.

12. The shaving cartridge of claim 1, comprising as a pyrithione source of about 0.5% zinc pyrithione, a pH adjusting agent of about 2% sodium carbonate, and further comprising as a zinc source of about 0.1% zinc carbonate.

13. The shaving cartridge of claim 1, wherein the polyoxyethylene has a molecular weight of from about 100,000 to about 5,000,000 and a silicone cross-polymer.

14. The shaving cartridge of 1, further comprising a silicone polymer selected from the group consisting of dimethicone PEG-7 panthenyl phosphate, dimethicone PEG-7 phosphate, dimethicone PEG-7 undecylenate, dimethicone/methicone copolymer, perfluoronoylethyl dimethicone methicone copolymer, dimethicone/vinyl dimethicone crosspolymer in dimethicone, vinyl dimethicone/lauryl dimethicone crosspolymer in mineral oil, vinyl dimethicone/lauryl dimethicone crosspolymer in squalane, vinyl dimethicone/methicone silsesquioxane crosspolymer, squalene and lauryl dimethicone/polyglycerin-3 crosspolymer, triethylhexanoin and lauryl dimethicone/polyglycerin-3 crosspolymer, and dimethicone/polyglycerin-3 crosspolymer and dimethicone, PEG/PPG-20/6 dimethicone, behenoxydimethicone, C24-28 alkyl methicone, dimethicone/vinyl dimethucine crosspolymer, and C12-C14 Pareth-12.

15. The shaving cartridge of claim 1, wherein the shaving aid portion further comprises a polyethylene, polybutene, and mineral oil composition.

16. The shaving cartridge of claim 1, wherein a first shaving aid is provided at the forward edge and a second shaving aid is provided at the rear edge, and wherein the second shaving aid comprises at least a portion of said pyrithione source.

* * * * *